United States Patent [19]

Dunn et al.

[11] Patent Number: 5,368,859
[45] Date of Patent: Nov. 29, 1994

[54] BIODEGRADABLE SYSTEM FOR REGENERATING THE PERIODONTIUM

[75] Inventors: Richard L. Dunn; Arthur J. Tipton; George L. Southard; Jack A. Rogers, all of Fort Collins, Colo.

[73] Assignee: Atrix Laboratories, Inc., Fort Collins, Colo.

[21] Appl. No.: 84,777

[22] Filed: Jun. 29, 1993

Related U.S. Application Data

[60] Continuation of Ser. No. 765,137, Sep. 25, 1991, abandoned, which is a division of Ser. No. 384,416, Jul. 24, 1989, Pat. No. 5,077,049.

[51] Int. Cl.$^5$ ............................................. A61F 2/00
[52] U.S. Cl. ............................... 424/426; 424/423; 424/424; 424/425; 424/435; 514/900
[58] Field of Search ............ 424/426, 423, 424, 425; 514/900

[56] References Cited

U.S. PATENT DOCUMENTS

| | | | |
|---|---|---|---|
| 3,068,188 | 12/1962 | Beste et al. | 524/173 |
| 3,919,773 | 11/1975 | Freeman | 433/201.1 |
| 3,949,073 | 4/1976 | Daniels et al. | 514/801 |
| 3,975,350 | 8/1976 | Hudgin et al. | 260/30.4 N |
| 4,451,452 | 5/1984 | Deibig et al. | 424/78 |
| 4,526,909 | 7/1985 | Urist | 523/115 |
| 4,563,489 | 1/1986 | Urist | 524/21 |
| 4,595,713 | 6/1986 | St. John | 424/423 |
| 4,596,574 | 6/1986 | Urist | 623/16 |
| 4,780,320 | 10/1988 | Baker | 424/493 |
| 4,863,472 | 9/1989 | Törmälä et al. | 433/201.1 |
| 4,905,680 | 3/1990 | Tunc | 606/69 |
| 4,912,141 | 3/1990 | Kronman | 424/423 |
| 4,919,939 | 4/1990 | Baker | 424/493 |
| 4,938,763 | 7/1990 | Dunn et al. | 604/891.1 |
| 4,961,707 | 10/1990 | Magnusson et al. | 433/215 |

FOREIGN PATENT DOCUMENTS 2223027 8/1989 United Kingdom.

OTHER PUBLICATIONS

K. Juni et al., *Control of Release Rate of Bleomycin From Polyactic Acid Microspheres by Additives*, Chem. Pharm. Bull. 33(4) 1609-1614 (1985).

Primary Examiner—Thurman K. Page
Assistant Examiner—James M. Spear
Attorney, Agent, or Firm—Merchant, Gould, Smith, Edell, Welter & Schmidt

[57] ABSTRACT

Methods are described for assisting the restoration of periodontal tissue in a periodontal pocket and for retarding migration of epithelial cells along the root surface of a tooth. The methods involve placement of an in-situ forming biodegradable barrier adjacent the surface of a tooth. The barrier is microporous and includes pores of defined size. The barrier can include a biologically active agent.

13 Claims, No Drawings

BIODEGRADABLE SYSTEM FOR REGENERATING THE PERIODONTIUM

This is a continuation of application Ser. No. 07/765,137, filed Sep. 25, 1991, abandoned, which is a divisional of Ser. No. 07/384,416, filed Jul. 24, 1989 now U.S. Pat. No. 5,077,049.

BACKGROUND OF THE INVENTION

Periodontal disease is a highly prevalent disease affecting 90% of the population. Surgery is one of the primary courses of therapy. It assists the patient in home management of the disease but does not result in the restoration of lost periodontium. If surgical therapy could be enhanced to restore the periodontium the patient benefits of the procedure would increase.

Successful periodontal restoration is known to occur if periodontal ligament cells are allowed to colonize root surfaces preferentially over gingival epithelial cells, gingival fibroblasts or osteoblasts. Several studies have been conducted which have elucidated this fundamental mechanism and illustrated its importance in obtaining successful periodontal restoration.

It has been demonstrated that microporous membranes applied beneath periodontal flaps during surgery physically occlude epithelial cells from apically migrating along the root surface. The subsequent recolonization of the root surface by gingival fibroblasts results in a more selective population of the root surface by periodontal ligament cells.

A number of membranes have been studied including a Millipore ® filter and a Teflon membrane. The Teflon membrane is marketed under the trademark GORE-TEX. A disadvantage of the Millipore ® and GORE-TEX ® membranes is the need for a second surgical entry to remove the membrane. Accordingly, a membrane for periodontal restoration that is biodegradable in the body would eliminate the need for a second surgical entry and be beneficial to the patient and surgeon from both cost and morbidity stand points.

The use of bioabsorbable membranes has been reported. These include microfibrillar collagen, a polygalactin (Vicryl ® mesh, and a polylactic acid membrane. Results achieved with these biodegradable membranes as well as the Millipore ® and GORE-TEX ® materials to induce guided tissue regeneration have been variable. Precise cutting of membranes and placement over the treatment site can be difficult, time consuming and unpredictable in therapeutic outcome. Higher incidence of infection has also been reported with the nonbiodegradable membranes. The collagen membranes have given variable degradation times in use and there is the concern for an immunological response to a foreign protein with this material.

There has not heretofore been provided a barrier membrane for tissue regeneration comprising a totally synthetic biodegradable material that can be placed in the repair site to form a membrane having the precise geometry needed for that location and the optimum porosity to prevent epithelial tissue downgrowth.

SUMMARY OF THE INVENTION

The present invention relates to the use of biodegradable polymers to promote guided tissue regeneration. These polymers can be uniquely administered in liquid form, for example, with a syringe and needle, brush, or pressure applicator to a periodontal pocket or surgical site. When administered the liquid system coagulates or cures(sets) in a short time to form a solid or gelatinous implant. Before the liquid system sets, the dental professional is able to manipulate the system to gain optimum conformity to the treatment site and overcome placement difficulties inherent in non-liquid systems.

The biodegradable liquid system is also,designed to generate a porous structure when coagulated or cured into the barrier membrane. In this respect, the membrane is similar to the Millipore ® and GORE-TEX ® membranes which have been shown to work in humans. It is also similar to the Vicryl ® mesh membrane except for the size of the pores. Based upon literature references and examination of the GORE-TEX ® membrane, a minimum pore size of about 3 microns and a maximum pore size of approximately 500 microns is needed for an effective tissue barrier product. If the pore size is too small, the epithelial cells simply grow around the barrier; if the pores are too large, the epithelial cells grow through the membrane and fill the defect with the wrong type of tissue. But with the correct pore size, the cells grow into the structure to a certain point where they are prevented from growing through or around the barrier. The connective tissue cells also grow into the microporous membrane and block any tendency for downward migration of epithelial cells. In addition, the porous barrier permits the diffusion of essential nutrients and growth factors to the area being repaired.

The number of pores or the percent porosity of the membrane has also been found to be critical to the success of the barrier in regenerating new tissue. If only a few pores are present, the cells that grow into the membrane will be unable to prevent epithelial migration and invagination of the membrane. If there are too many pores, then the membrane will have little structural integrity and it will fracture in use. When this occurs, the membrane does not promote a barrier to cell migration. Consequently, the porous structure described in the present invention is essential to proper tissue regeneration end substantially different from the polylactic acid membranes described in the literature. The membrane-forming biodegradable liquid polymer system and the porous structure of the biodegradable polymer membrane represent a new and improved system over that of previous synthetic biodegradable polymer membranes for periodontal tissue regeneration.

The membrane-forming liquid polymer systems are formulated from biodegradable polymers and copolymers comprising thermoplastic and thermosetting polymer systems. A thermoplastic system is provided in which a solid biodegradable polymer or copolymer is dissolved in a solvent, which is nontoxic and water miscible, to form a liquid solution. Once the polymer solution is placed into the body where there is sufficient water, the solvent dissipates or diffuses away from the polymer, leaving the polymer to coagulate or solidify into a solid structure which can serve as a barrier membrane. Alternatively, the liquid can be set outside of the body so that the dental professional can shape the material to fit the site of application. To obtain the porous structure needed for optimum barrier properties, water-soluble materials are incorporated into the polymer solution. These water-soluble materials may be solid particles such as sugar or salt crystals, polymers not soluble in the biodegradable polymer or its carder solvent, or polymers that are also soluble in the solvent for the biodegradable polymer.

Biologically active agents can also be incorporated into the polymer to provide a porous structure as well as to produce a biological effect. For these systems, the biologically active agent is added to the polymer solution where it is either dissolved to form a homogeneous solution or dispersed to form a suspension or dispersion of drug within the polymeric solution. When the polymer solution is exposed to body fluids or water, the solvent diffuses away from the polymer-drug mixture and water diffuses into the mixture where it coagulates the polymer thereby trapping or encapsulating the drug within the polymeric matrix as the implant solidifies. The release of the drug then follows the general rules for diffusion or dissolution of a drug from within the polymeric matrix. The dissolution of the biologically active agent creates pores in the polymer membrane into which the cells can penetrate. The size of the pores generated is dependent upon the particle size of the drug or the water-soluble particle if the material is dispersed within the polymer matrix. If the drug or material is soluble in the polymer solution, then the quantity and the uniformity of the distribution of the material within the polymer matrix as the polymer coagulates will determine the size of the pores when the agent or material is released or dissolved out of the solid polymer matrix.

The other liquid polymer system which can be used to generate the barrier membrane in-situ is a thermosetting system comprising reactive, liquid, oligomeric polymers which contain no solvents and which cure in place to form solids, usually with the addition of a curing catalyst. The liquid oligomeric polymers useful in the thermosetting system are first synthesized via copolymerization of either DL-lactide or L-lactide with ε-caprolactone using a multifunctional polyol initiator and a catalyst to form polyol-terminated prepolymers. The polyol-terminated prepolymers are then converted to acrylic ester-terminated prepolymers, preferably by acylation of the alcohol terminus with acryloyl chloride via a Schotten-Baumann-like technique, i.e., reaction of acyl halides with alcohols. The acrylic ester-terminated prepolymers may also be synthesized in a number of other ways, including but not limited to, reaction of carboxylic acids i.e., acrylic or methacrylic acid with alcohols, reaction of carboxylic acid esters i.e., methyl acrylate or methyl methacrylate with alcohols by transesterification, and reaction of isocyanatoalkyl acrylates i.e., isocyanatoethyl methacrylate with alcohols.

The liquid acrylic-terminated prepolymer is cured, preferably by the addition of benzoyl peroxide or azobisisobutyronitile, to a more solid structure, Thus, for a barrier membrane utilizing these crosslinkable polymers, the catalyst is added to the liquid acrylic-terminated prepolymer immediately prior to injection into the body. Once in the repair site, the crosslinking reaction will proceed until sufficient molecular weight has been obtained to cause the polymer to solidify and form the barrier membrane. The liquid prepolymer can also be formed and cured outside of the tissue repair site to give a membrane with the exact dimensions needed for that location. The thermosetting polymers may be made porous by the same techniques described above for the thermoplastic polymers. Water-soluble components such as sodium chloride, sodium carbonate, sugar, citric acid, and polymers such as poly(vinyl pyrrolidone) and poly(ethylene glycol) may be incorporated into the liquid prepolymer before it is cured. Biologically active agents that release or dissolve out of the solid polymer matrix may also be used to create a porous structure as well as a biological effect.

In both the thermoplastic and the thermosetting systems, the advantages of liquid application are achieved. For example, the polymer may be injected via syringe and needle into the periodontal pocket or surgical site while it is in liquid form and then left in-situ to form a solid, microporous, biodegradable barrier membrane or implant structure. Alternatively, the liquid system can be set outside of the body so it can be shaped or molded to a site. In addition to providing a porous barrier membrane, those liquid polymers containing biologically active agents may be used to stimulate or accelerate tissue repair by serving as a drug delivery vehicle also. As such, the liquid polymer may be injected directly into the area of tissue needing repair. The release of the active agents will stimulate cellular activity and the porous structure of the implant will allow tissue ingrowth and subsequent tissue repair as the polymer biodegrades.

The term "biologically active agent" means a drug or some other substance capable of producing a physiological effect on a body. Drugs suitable for the purpose of restoring the periodontium are of synthetic and natural origin. Such drugs are termed tissue repair mediators and include but are not limited to fibronectin(FN), endothelial cell growth factor(ECGF), cementum attachment extracts(CAE), ketanserin, human growth hormone(HGH), animal growth hormones, fibroblast growth factor(FGF), platelet derived growth factor(PDGF), epidermal growth factor(EGF), interleukin-1 (IL-1), transforming growth factor(TGFβ-2), insulin-like growth factor II(ILGF-II), human alpha thrombin(HAT), osteoinductive factor(OIF), bone morphogenetic protein(BMP), and releasing factors for any of the above. The interaction of these biochemical mediators and cellular extracts with regenerative cells has been discussed in the literature. Other drugs such as antibiotics or antimicrobial agents can also added to the liquid polymer to give membranes or implants which prevent an infection.

It is an object of the present invention to provide a method to aid in the restoration of the periodontium through guided tissue regeneration by physical barrier means.

It is also an object of the present invention to provide a method to aid in the restoration of the periodontium by sewing as a controlled release delivery system for mediators that stimulate periodontal tissue repair.

It is also an object of the present invention to provide a method to assist in the restoration of the periodontium simultaneously through guided tissue regeneration by barrier means and the controlled release of mediators that stimulate periodontal tissue repair.

It is also an object of the present invention to provide an in-situ forming microporous implant to serve as a physical barrier or delivery system for tissue repair mediators.

It is also an object of this invention to provide a method to prevent infection by the incorporation of antimicrobial agents into the system while aiding in the restoration of the periodontium through physical barrier means and/or the delivery of tissue repair mediators.

DETAILED DESCRIPTION OF THE INVENTION

The present invention relates to in-situ forming biodegradable microporous membranes or implants that can be used to aid in the restoration of the periodontium by the principal of guided tissue regeneration and/or delivery of biochemical mediators to restore the periodontium. Two types of biodegradable polymers described for these purposes are thermoplastic polymers dissolved in a biocompatible solvent and thermosetting polymers that are liquids without the use of solvents.

A. Thermoplastic System

A thermoplastic system is provided in which a solid, linear-chain, biodegradable polymer is dissolved in a biocompatible solvent to form a liquid, which can then be administered via a syringe and needle. Examples of biodegradable polymers which can be used in this application are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of the above materials. The preferred polymers are those which have lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with each other and glycolide in which there are more amorphous regions to enhance solubility.

It is also preferred that the solvent for the biodegradable polymer be non-toxic, water miscible, and otherwise biocompatible. Solvents that are toxic should not be used to inject any material into a living body. The solvents must also be biocompatible so that they do not cause severe tissue irritation or necrosis at the site of implantation. Furthermore, the solvent should be water miscible so that it will diffuse quickly into the body fluids and allow water to permeate into the polymer solution and cause it to coagulate or solidify. Examples of such solvents include N-methyl-2-pyrrolidone, 2-pyrrolidone, ethanol, propylene glycol, acetone, methyl acetate, ethyl acetate, ethyl lactate, methyl ethyl ketone, dlmethylformamide, dimethyl sulfoxide, dimethyl sulfone, tetrahydrofuran, caprolactam, decylmethylsulfoxide, oleic acid, N,N-diethyl-m-toluamide, and 1-dodecylazacycloheptan-2-one. The preferred solvents are N-methyl-2-pyrrolidone, 2-pyrrolidone, dimethyl sulfoxide, and acetone because of their solvating ability and their compatibility.

The solubility of the biodegradable polymers in the various solvents will differ depending upon their crystallinity, their hydrophibicity, hydrogen-bonding, and molecular weight. Thus, not all of the biodegradable polymers will be soluble in the same solvent, but each polymer or copolymer should have its optimum solvent. Lower molecular-weight polymers will normally dissolve more readily in the solvents than high-molecular-weight polymers. As a result, the concentration of a polymer dissolved in the various solvents will differ depending upon type of polymer and its molecular weight. Conversely, higher molecular-weight polymers will normally tend to coagulate or solidify faster than the very low-molecular-weight polymers. Moreover the higher molecular-weight polymers will tend to give higher solution viscosities than the low-molecular-weight materials. Thus for optimum injection efficiency, the molecular weight and the concentration of the polymer in the solvent have to be controlled.

For polymers that tend to coagulate slowly, a solvent mixture can be used to increase the coagulation rate. Thus one liquid component of the mixture is a good solvent for the polymer, and the other component is a poorer solvent or a non-solvent. The two liquids are mixed at a ratio such that the polymer is still soluble but precipitates with the slightest physiological environment. By necessity, the solvent system must be miscible with both the polymer and water.

In one envisioned use of the thermoplastic system, the polymer solution is placed in a syringe and injected through a needle into the periodontal site. Once in place, the solvent dissipates, the remaining polymer solidifies, and a solid structure such as a membrane or implant is formed. The polymer will adhere to the surrounding tissue or bone by mechanical forces and can assume the shape of the periodontal pocket or surgical site. Unlike collagen implants, the degradation time of the polymer can be varied from a few weeks to years depending upon the polymer selected and its molecular weight. The injectable system can also be used to adhere gingival tissue to other tissue or other implants to tissue by virtue of its mechanical bonding. Another envisioned use of the liquid polymer system is to provide a drug-delivery system. In this use, a bioactive agent is added to the polymer solution prior to injection, and then the polymer/solvent/agent mixture is injected into the body. In some cases, the drug will also be soluble in the solvent, and a homogenous solution of polymer and drug will be available for injection. In other cases, the drug will not be soluble in the solvent, and a suspension or dispersion of the drug in the polymer solution will result. This suspension or dispersion can also be injected into the body. In either case, the solvent will dissipate and the polymer will solidify and entrap or encase the drug within the solid matrix. The release of drug from these solid implants will follow the same general rules for release of a drug from a monolithic polymeric device. The release of drug can be affected by the size and shape of the implant, the loading of drug within the implant, the permeability factors involving the drug and the particular polymer, the porosity of the polymer implant or membrane, and the degradation of the polymer. Depending upon the bioactive agent selected for delivery, the above parameters can be adjusted by one skilled in the art of drug delivery to give the desired rate and duration of release.

The term drug or bioactive (biologically active) agent as used herein includes without limitation physiologically or pharmacologically active substances that act locally or systemically at a periodontal site. Representative drugs and biologically active agents to be used with the syringeable, in-situ forming, solid microporous implant systems include, without limitation, FN, ECGF, CAE, ketanserin, HGH, animal growth hormones, FGF, PDGF, EGF, IL-1, TGF$\beta$-2 ILGF-II, HAT, OIF, BMP, and releasing factors for any of the above. Antimicrobial agents and antibiotics can also be used. To those skilled in the art, other drugs or biologically active agents that can be released in an aqueous environment can be utilized in the described injectable delivery system. Also, various forms of the drugs or biologically active agents may be used. These include without limitation forms such as uncharged molecules, molecular complexes, salts, ethers, esters, amides, etc., which are biologically activated when injected into the body.

The amount of drug or biologically active agent incorporated into the injectable, in-situ, solid forming implant depends upon the desired release profile, the concentration of drug required for a biological effect, and the length of time that the drug has to be released for treatment. There is no critical upper limit on the amount of drug incorporated into the polymer solution except for that of an acceptable solution or dispersion viscosity. The lower limit of drug incorporated into the delivery system is dependent simply upon the activity of the drug and the length of time needed for treatment.

Not only can the drug incorporated into the system be used to create a biological effect, but it can also be used to create the microporous structure needed for connective tissue ingrowth and barrier to epithelial migration. If the drug is highly water soluble, it will be dissolved or released from the polymer matrix quickly and create the pores required for tissue ingrowth. If the drug is released or dissolved slowly, the pores can be created at a rate similar to that for cell migration into the newly formed pores. The size of the pores will be dependent upon the size of the drug particles in the polymer matrix. If the drug is insoluble in the polymer formulation, then discrete particles of drug can be properly sized or sieved before incorporation into the polymer solution to give the desired pore size. If the drug is also soluble in the polymer solution, then the distribution or mixing of the drug within the formulation and the method by which the drug precipitates upon contact with water of body fluids will determine the pore sizes when the precipitated particles are later dissolved. The pore sizes can be determined by examining cross-sections of the coagulated polymer matrix with scanning electron microscopy. An average pore size and distribution can be calculated from these examinations. For an effective tissue barrier, the pore sizes should be a minimum of 3 microns and less than 500 microns. The preferred pore sizes should range from about 20 to 200 microns.

The number of pores or the percent porosity will depend upon the quantity of water-soluble drug or other water-soluble ingredients incorporated into the formulation. Larger quantities of such materials will provide more pores and a higher percent porosity. The percent porosity should be between 5% and 95% with the preferable range of 25 to 85% for optimum tissue ingrowth and structural integrity. The percent porosity can be determined by a number of different methods including mercury intrusion porosimetry, specific gravity or density comparisons, and calculations from scanning electron microscopy photographs. To simplify the determination of porosity in our system, we have defined percent porosity as the percent water-soluble material present in the formulation. This calculation is appropriate because the polymer forms a membrane as soon as it contacts body fluid or water and the dissolution of the water-soluble materials including the solvent, creates pores. Thus, a formulation that contains 30% polymer and 70% solvent or other water-soluble material would provide a solid polymer matrix with 70% porosity.

Pores can also be created in the polymer matrix by the use of water-soluble compounds that are not drugs. Almost any biocompatible water-soluble material can be used. These materials can either be soluble in the polymer solution or simply dispersed within the formulation. The same parameters described above for the drugs govern the pore size and percent porosity obtained with these nondrug materials. Thus, the size of the particles dispersed within the polymer formulation determine the size of the resulting pores in the solidified polymer matrix and the quantity of material determines the percent porosity. If the material is soluble in the polymer formulation, then the mixing or distribution of the material in the polymer solution and the aggregation when the polymer coagulates will determine the size of the resultant pores when the material dissolves out of the polymer matrix. A number of different water-soluble materials can be dispersed or dissolved in the polymer formulation to give pores when they are slowly dissolved in the body. These include sugars, salts, and polymers. Examples are sucrose, dextrose, sodium chloride, sodium carbonate, hydroxylpropylcellulose, carboxymethylcellulose, polyethylene glycol, and polyvinylpyrrolidone.

In all cases, the microporous solid implant formed with the injectable polymer solution will slowly biodegrade within the periodontal site and allow natural tissue to grow and replace the implant as it disappears. Thus, when the material is injected into a soft-tissue defect, it will fill that defect and provide a scaffold for natural collagen tissue to grow. This collagen tissue will gradually replace the biodegradable polymer. With hard tissue such as bone, the biodegradable polymer will support the growth of new bone cells which will also gradually replace the degrading polymer. For drug-delivery systems, the solid microporous implant formed from the injectable system will release the drug contained within its matrix at a controlled rate until the drug is depleted. With certain drugs, the polymer will degrade after the drug has been completely released. With other drugs such as peptides or proteins, the drug will be completely released only after the polymer has degraded to a point where the non-diffusing drug has been exposed to the body fluids.

B. Thermosetting System

The injectable, in-situ forming, biodegradable microporous implants can also be produced by crosslinking appropriately functionalized biodegradable polymers. The thermosetting system comprises reactive, liquid, oligomeric polymers which cure in place to form solids, usually with the addition of curing catalyst. Although any of the biodegradable polymers previously described for the thermoplastic system can be used, the limiting criteria is that low-molecular-weight oligomers of these polymers or copolymers must be liquids and they must have functional groups on the ends of the prepolymer which can be reacted with acryloyl chloride to produce acrylic-ester-capped prepolymers.

The preferred biodegradable system is that produced from poly(DL-lactide-caprolactone), or "DL-PLC". Low-molecular-weight polymers or oligomers produced from these materials are flowable liquids at room temperature. Hydroxy-terminated PLC prepolymers may be synthesized via copolymerization of DL-lactide or L-lactide and ε-caprolactone with a multifunctional polyol initiator and a catalyst. Catalysts useful for the preparation of these prepolymers are preferably basic or neutral ester-interchange (transesterification) catalysts. Metallic esters of carboxylic acids containing up to 18 carbon atoms such as formic, acetic, lauric, stearic, and benzoic are normally used as catalysts. Stannous octoate and stannous chloride are the preferred catalysts, both for reasons of FDA compliance and performance.

If a bifunctional polyester is desired, a bifunctional chain initiator such as ethylene glycol is employed. A trifunctional initiator such as trimethylolpropane produces a trifunctional polymer, etc. The amount of chain initiator used determines the resultant molecular weight of the polymer or copolymer. At high concentrations of chain initiator, the assumption is made that one bifunctional initiator molecule initiates only one polymer chain. On the other hand, when the concentration of bifunctional initiator is very low, each initiator molecule can initiate two polymer chains. In any case, the polymer chains are terminated by hydroxyl groups, in this example, the assumption has been made that only one polymer chain is initiated per bifunctional initiator molecule. This assumption allows the calculation of theoretical molecular weight for the prepolymers.

The diol prepolymers are converted to acrylic-ester-capped prepolymers via a reaction with acryloyl chloride under Schotten-Baumann-like conditions. Other methods of converting the diol prepolymers to acrylic-ester-capped prepolymers may also be employed.

The acrylic prepolymers and diol prepolymers are then cured. The general procedure for the curing of the prepolymers is now described: to 5.0 g of acrylic prepolymer contained in a small beaker is added a solution of benzoyl peroxide (BP) in approximately 1 mL of $CH_2Cl_2$. In some cases, fillers or additional acrylic monomers may be added to the prepolymers prior to the introduction of the BP solution. The mixtures are stirred thoroughly and then poured into small petri dishes where they are cured at room temperature in air or in a preheated vacuum oven.

This thermosetting system may be used wherever a biodegradable implant is desired. For example, because the prepolymer remains a liquid for a short time after addition of the curing agent, the liquid prepolymer/curing agent mixture may be placed into a syringe and injected into a body. The mixture then solidifies in-situ, thereby providing an implant without an incision. The mixture may also be placed into an incision without the use of a syringe to form a membrane or implant. Furthermore, a drug-delivery system may be provided by adding a biologically active agent to the prepolymer prior to injection. Once in-situ, the system will cure to a solid; eventually, it will biodegrade, and the agent will be gradually released. A microporous structure may be formed by the dissolution or release of the biologically active agent, or water-soluble materials may be incorporated into the liquid prepolymer before it is injected into the body and cured. The same parameters described for the thermoplastic system also govern the size of the pores formed in the implant and the percent porosity.

DETAILED DESCRIPTION OF EXAMPLES

The following examples are set forth as representative of the present invention. These examples are not to be construed as limiting the scope of the invention as these and other equivalent embodiments will be apparent in view of the present disclosure, figures, and accompanying claims.

EXAMPLE 1

A formulation consisting of a 5% equimolar mixture of sodium carbonate and citric acid, 34.8% poly(DL-lactide) (DL-PLA) and 60.2% N-methyl pyrrolidone (NMP) was prepared by suspending the particles of the sodium carbonate and citric acid in the polymer solution. The DL-PLA polymer had a molecular weight of about 30,000 daltons (inherent viscosity of 0.38 dL/g). One drop of the formulation was precipitated into a vial containing phosphate-buffered saline (PBS) or water. The vial was placed in a 37° C. shaker bath. After remaining at 37° C. for a time period of at least 48 h, the sample was removed from the fluid, and dried in vacuo prior to examination by SEM. A porous structure resulted with 5μ pores and a percent porosity of 65.2%.

EXAMPLE 2

A formulation consisting of 5% sucrose, 34.8% DL-PLA and 60.2% NMP was treated as in Example 1. A porous structure resulted with a large number of 314 pores and a percent porosity of 65.2%.

EXAMPLE 3

A formulation consisting of 5% poly(vinyl pyrrolidone)(PVP), 34.8% DL-PLA and 60.2% NMP was treated as in Example 1. A porous structure resulted with pore sizes of 5–10μ and a percent porosity of 65.2%.

EXAMPLE 4

A formulation consisting of 10% PVP, 33.0% DL-PLA and 57.0% NMP was treated as in Example 1. A porous structure resulted with pore sizes of 5–20μ and a percent porosity of 67.0%.

EXAMPLE 5

A formulation was prepared consisting of 50% DL-PLA and 50% NMP with two different molecular weights of polymer. A water-soluble low-molecular-weight DL-PLA with a molecular weight of 2000 daltons was mixed with e higher-molecular-weight DL-PLA with an inherent viscosity of 0.38 dL/g and an approximate molecular weight of 30,000 daltons and dissolved in NMP to give a solution with a composition of 38% low-molecular-weight DL-PLA, 12% higher molecular weight DL-PLA, and 50% NMP. This formulation was treated as described in Example 1 to give a porous structure with pores from 10–50μ and a percent porosity of 50%.

EXAMPLE 6

A formulation consisting of 5% ethoxydihydrosanguinarine (SaOEt), 27.5% DL-PLA and 67.5% NMP was treated as in Example 1. SaOEt is an antimicrobial agent derived from the benzophenanthridine alkaloids. A porous structure resulted with pore sizes of 15–30μ and a percent porosity of 72.5%.

EXAMPLE 7

A formulation consisting of 5% SaOEt, 27.5% DL-PLA and 67.5% NMP was treated as in Example 1. The difference was that the DL-PLA used in this sample had a lower molecular weight of about 10,000 daltons. A porous structure resulted with pore size of 4–8μ. This sample was also examined by X-ray tomography on a wet sample. Scanned at intervals of 0–25 ram, the samples showed porosity throughout with a percent porosity of 72.5%.

EXAMPLE 8

A formulation consisting of 5.0% sanguinarine chloride (SaCl), 47.5% DL-PLA and 47.5% NMP was placed in the periodontal pocket of a human. SaCl is an antimicrobial and anti-inflammatory agent derived from the benzophenathridine alkaloids. After 28 days the samples was removed, dried in vacuo and examined by SEM. Small pores of 1–2$\mu$ and larger pores of 10–20$\mu$ were evident with a percent total porosity of 52.5%. Approximately 50% of the pores were 10–20$\mu$.

EXAMPLE 9

A formulation consisting of 33% PVP, 33% 50/50 copolymer of DL-lactide and glycolide (DL-PLG) and 34% NMP was treated as in Example 1. A porous structure, resulted with pore sizes of 3–10$\mu$. Further examination showed the pores in an interconnecting network with a percent porosity of 67%.

EXAMPLE 10

A lypholized sample of fibronectin, a tissue growth and cell attachment factor, was added to a solution of DL-PLA in NMP to give a dispersion with 13.2% by weight of the lypholized fibronectin product, 30.4% DL-PLA, and 56.4% NMP. Because the fibronectin product contained various salts as a result of the lypholization process, there was only 0.89% of active drug in the formulation. This formulation was added to a phosphate-buffered receiving fluid where it coagulated into a solid mass. The receiving fluid was maintained at 37° C. under agitation and changed often to prevent a high concentration of the drug in the fluid. The receiving fluid was analyzed for total protein concentration by the Pierce BCA protein assay and the cumulative percentage of drug released was calculated. After one day, about 12% of the drug was released with 25% after 2 days, 26% after 3 days, 28% after 4 days, 30% after 5 days, and 33% after 7 days. The percent porosity of the initial implant was 56.4% with the level increasing as the drug was released. The pores produced were greater than 3$\mu$.

EXAMPLE 11

Ketanserin tartrate, a serotonin antagonist and wound-healing factor, was added to a solution of DL-PLA in NMP to give a clear solution containing 10% by weight ketanserin, 33% DLPLA, and 57% NMP. When this formulation was added to phosphate-buffered saline solution (pH 7.1), it coagulated into a solid mass. The receiving fluid was maintained at 37° C. under agitation and exchanged frequently. It was noted that as the ketanserin released from the polymer it precipitated in the buffered saline solution. The precipitated drug was filtered and dissolved in dlmethylformamide for analysis by HPLC. The release of ketanserin was essentially constant throughout the period of observation with about 0.8% after 1 day, 3.2% after 6 days, and 7.3% after 16 days. The percent porosity of the initial implant was 57% and the pore size was 5–15$\mu$. The percent porosity increased as the drug was released from the polymer matrix.

What is claimed is:

1. A method for assisting the restoration of periodontal tissue in a periodontal pocket, comprising:
placing a liquid mixture of a biodegradable, curable, thermosetting prepolymer, curing agent and a water-soluble material into the periodontal pocket; wherein the water-soluble material dissipates into periodontal fluids, the thermosetting prepolymer cures in situ by formation of covalent bonds to form a water-immiscible thermoset polymer as a solid biodegradable implant, and the dissipation of the water-soluble material creates pores within the solid biodegradable implant having sizes in the range of about 3 to about 500 microns, the solid biodegradable implant having a porosity in the range of about 5 to 95 percent provided by the pores, and the sizes of the pores and porosity being effective to promote cell growth.

2. A method in accordance with claim 1, wherein said implant includes pores having a size in the range of 20 to 200 microns.

3. A method in accordance with claim 1, wherein said water-soluble material is selected from the group consisting of sugars, salts, and water-soluble polymers.

4. A method in accordance with claim 1, wherein said water-soluble material is present in an amount of about 5 to 85 percent by weight based upon the weight of said polymer.

5. A method in accordance with claim 1, wherein said implant further comprises a biologically active agent selected from the group consisting of antimicrobial agents, antibiotics and tissue repair mediators.

6. A method in accordance with claim 1, wherein said thermosetting prepolymer is an acrylic-ester-terminated prepolymer and a curing agent is added to said prepolymer prior to placing the mixture.

7. A method in accordance with claim 6, wherein said prepolymer comprises poly(DL-lactide-co-caprolactone).

8. A method for retarding apical migration of epithelial cells along a root surface of a tooth comprising placing a liquid mixture of a biodegradable, curable, thermosetting prepolymer, curing agent and water-soluble material into said periodontal pocket; wherein said water-soluble material dissipates into periodontal fluids and the curable thermosetting prepolymer cures in situ to form a water-immiscible thermoset polymer as a solid biodegradable barrier adjacent to said surface, and said dissipation of the water-soluble material creates pores within said solid biodegradable barrier having sizes in the range of about 3 to about 500 microns; said solid biodegradable barrier having porosity in the range of 5 to 95% provided by said pores; and the sizes of said pores and porosity being effective to promote cell growth.

9. A method in accordance with claim 8, wherein said thermosetting prepolymer is an acrylic-ester-terminated prepolymer and a curing agent is added to said prepolymer prior to placing the mixture.

10. A method in accordance with claim 9, wherein said prepolymer comprises poly(DL-lactide-co-caprolactone).

11. A method for promoting guided tissue regeneration in a periodontal pocket comprising: placing a liquid mixture of a biodegradable, curable, thermosetting prepolymer, curing agent and a water-soluble material into a periodontal pocket; wherein said water-soluble material dissipates into periodontal fluids and said thermosetting prepolymer cures in-situ to form a water-immiscible thermoset polymer as a solid biodegradable implant, and said dissipation of the water-soluble material creates pores within said solid biodegradable implant having sizes in the range of about 3 to 500 microns; said biodegradable implant having a porosity in the range of 5% to 95% provided by said pores; and the sizes of said pores and porosity being effective to create cell growth.

12. A method in accordance with claim 11, wherein said thermosetting prepolymer is an acrylic-ester-terminated prepolymer and a curing agent is added to said prepolymer prior to placing the mixture.

13. A method in accordance with claim 12, wherein said prepolymer comprises poly(DL-lactide-co-caprolactone).

* * * * *

UNITED STATES PATENT AND TRADEMARK OFFICE
CERTIFICATE OF CORRECTION

PATENT NO. : 5,368,859

DATED : Nov. 29, 1994

INVENTOR(S) : Dunn et al.

It is certified that error appears in the above-identified patent and that said Letters Patent is hereby corrected as shown below:

At Col. 2, Line 41, delete "end" and insert therefor --and--.

At Col. 2, Line 66, delete "carder" and insert therefor --carrier--.

At Col. 4, Line 51, delete "sewing" and insert therefor --serving--.

At Col. 5, Line 61, delete "hydrophibicity" and insert therefor --hydrophilicity--.

At Col. 8, Line 62, delete "(DL-lactide-caprolactone)" and insert therefor --(DL-lactide-co-caprolactone)--.

At Col. 10, Line 21, delete "314" and insert therefor --3$\mu$--.

At Col. 10, Line 68, delete "0-25 ram" and insert therefor --0-25mm--.

At Col. 11, Line 51, delete "DLPLA" and insert therefor --DL-PLA--.

Signed and Sealed this

Twenty-seventh Day of February, 1996

Attest:

BRUCE LEHMAN

*Attesting Officer*     *Commissioner of Patents and Trademarks*